(12) United States Patent
Michalik

(10) Patent No.: US 9,089,623 B2
(45) Date of Patent: Jul. 28, 2015

(54) ELECTROMAGNETIC WAVE STERILIZATION

(71) Applicant: Maguffin Microwave LLC, Andover, MA (US)

(72) Inventor: Richard Michalik, Andover, MA (US)

(73) Assignee: Maguffin Microwave LLC, Andover, MA (US)

( * ) Notice: Subject to any disclaimer, the term of this patent is extended or adjusted under 35 U.S.C. 154(b) by 141 days.

(21) Appl. No.: 13/894,667

(22) Filed: May 15, 2013

(65) Prior Publication Data

US 2013/0315785 A1 Nov. 28, 2013

Related U.S. Application Data

(60) Provisional application No. 61/648,224, filed on May 17, 2012.

(51) Int. Cl.
| | |
|---|---|
| G01N 21/00 | (2006.01) |
| A61N 5/00 | (2006.01) |
| A61B 1/00 | (2006.01) |
| A61L 2/20 | (2006.01) |
| A61M 39/10 | (2006.01) |
| A61L 2/12 | (2006.01) |
| A61M 39/16 | (2006.01) |
| A61M 39/18 | (2006.01) |
| A61L 2/10 | (2006.01) |

(52) U.S. Cl.
CPC ... *A61L 2/20* (2013.01); *A61L 2/12* (2013.01); *A61M 39/10* (2013.01); *A61M 39/16* (2013.01); *A61M 39/18* (2013.01); *A61L 2/10* (2013.01)

(58) Field of Classification Search
CPC ........ A61L 2/00; A61L 2/0017; B08B 7/0035
USPC ...................... 422/21–24, 28, 295, 300, 307; 250/432 R, 455.11, 492.1, 505.1; 600/133; 604/533
See application file for complete search history.

(56) References Cited

U.S. PATENT DOCUMENTS

| | | | |
|---|---|---|---|
| 4,614,514 A | * | 9/1986 | Carr et al. ..................... 604/113 |
| 5,552,112 A | | 9/1996 | Schiffmann et al. |
| 5,858,303 A | | 1/1999 | Schiffmann et al. |
| 7,004,775 B1 | | 2/2006 | Sakurai et al. |

* cited by examiner

*Primary Examiner* — Monzer R Chorbaji
(74) *Attorney, Agent, or Firm* — Occhiuti & Rohlicek LLP

(57) ABSTRACT

An apparatus for sterilizing a fluid fitting includes a microwave source disposed in a shielded chamber, a pressure chamber inside the shielded chamber for receiving the luer lock and a sterilizing medium. The pressure chamber is in microwave communication with the microwave source. The apparatus also includes mechanical fluid clamps at each end of the pressure chamber for enabling pressurization of the pressure chamber.

19 Claims, 6 Drawing Sheets

ELECTROMAGNETIC WAVE STERILIZATION

CROSS-REFERENCE TO RELATED APPLICATIONS

This application claims the priority of U.S. Provisional Application No. 61/648,224, filed on May 17, 2012. The contents of the application are hereby incorporated by reference in its entirety.

FIELD OF DISCLOSURE

This disclosure relates to microwave heating, and in particular, to devices and methods for sterilization.

BACKGROUND

Intravenous medical fluid delivery involves hooking up external fluids and tubing to a device installed on the patient. Sometimes the device is semi-permanently attached to the patient, as in the case of dialysis. The connection to of the attached device to the external tubing/fluids is typically a Luer Lock/Fitting.

A current method for cleaning such a device is for a nurse to apply an alcohol soaked cotton ball to all accessible surfaces. This method is sometimes ineffective, as many patients become sick immediately after the process due to biological contaminants introduced.

It is known to use microwave devices to sterilize plastic tubing, luer locks, or other small medical devices designed for use in providing intravenous fluids to a patient. Known devices are either table-mounted or require placing the entire plastic unit inside the device. Examples of such devices are disclosed in U.S. Pat. No. 5,552,112 and U.S. Pat. No. 5,858,303.

Devices for heating up liquid trapped in a small section of intravenous tubing, including in a luer lock, have been previously proposed, for example in U.S. Pat. No. 4,614,514. But the system was a large bench mounted unit.

It is also known to use handheld devices for microwave curing of polymer materials in dentistry applications, an example of which is found in U.S. Pat. No. 7,004,775.

SUMMARY

The invention disclosed herein provides a better way for cleaning a Luer Lock and any immediately surrounding tubing, as well as for cleaning a fluid fitting generally.

In one aspect, the invention features an apparatus for sterilizing a fluid fitting. Such an apparatus includes a microwave source disposed in a shielded chamber, a pressure chamber inside the shielded chamber for receiving the luer lock and a sterilizing medium, the pressure chamber being in microwave communication with the microwave source, and mechanical fluid clamps at each end of the pressure chamber for enabling pressurization of the pressure chamber.

Embodiments of the invention includes those that have a phase-change material disposed under the microwave source for absorbing energy from the shielded chamber for disposal outside the shielded chamber.

In other embodiments, an infra-red temperature sensor monitors a temperature of the sterilizing medium within the pressure chamber.

Among the embodiments are those that also include a spatial location of a focal point of the microwave energy within the pressure chamber.

In at least one embodiment, the apparatus includes a low-pass filter disposed to suppress leakage of microwave radiation. Such a filter can include a microwave choke having joints filled with a dielectric material having a dielectric constant relative to fee space of at least fifteen. In alternative embodiments the low-pass filter includes a microwave choke having an outer ring shielded by a dielectric material loaded with iron, or the low-pass filter includes a microwave choke having an outer ring shielded by a dielectric material loaded with carbon.

In additional embodiments, the microwave source includes a self-oscillating transistor.

These and other features of the invention will be apparent from the following detailed description and the accompanying figures, in which:

DETAILED DESCRIPTION

A better method for cleaning a Luer Lock is to place some water or saline solution in it, capture it in a small area, and apply microwave heating energy to it. If a sufficiently high temperature is reached for a sufficient time duration, then the bio-burden is significantly reduced. If additional time and temperature is applied, then an actual sterilization may be achieved. As used herein, both bio-burden reduction and actual sterilization will be referred to as "sterilization."

To achieve the temperatures required, the pressure in the liquid is best increased to be above standard atmospheric pressure of 1 atmosphere. In some embodiments, the pressure is as high as 2 to 3 atmospheres.

Figure 1:
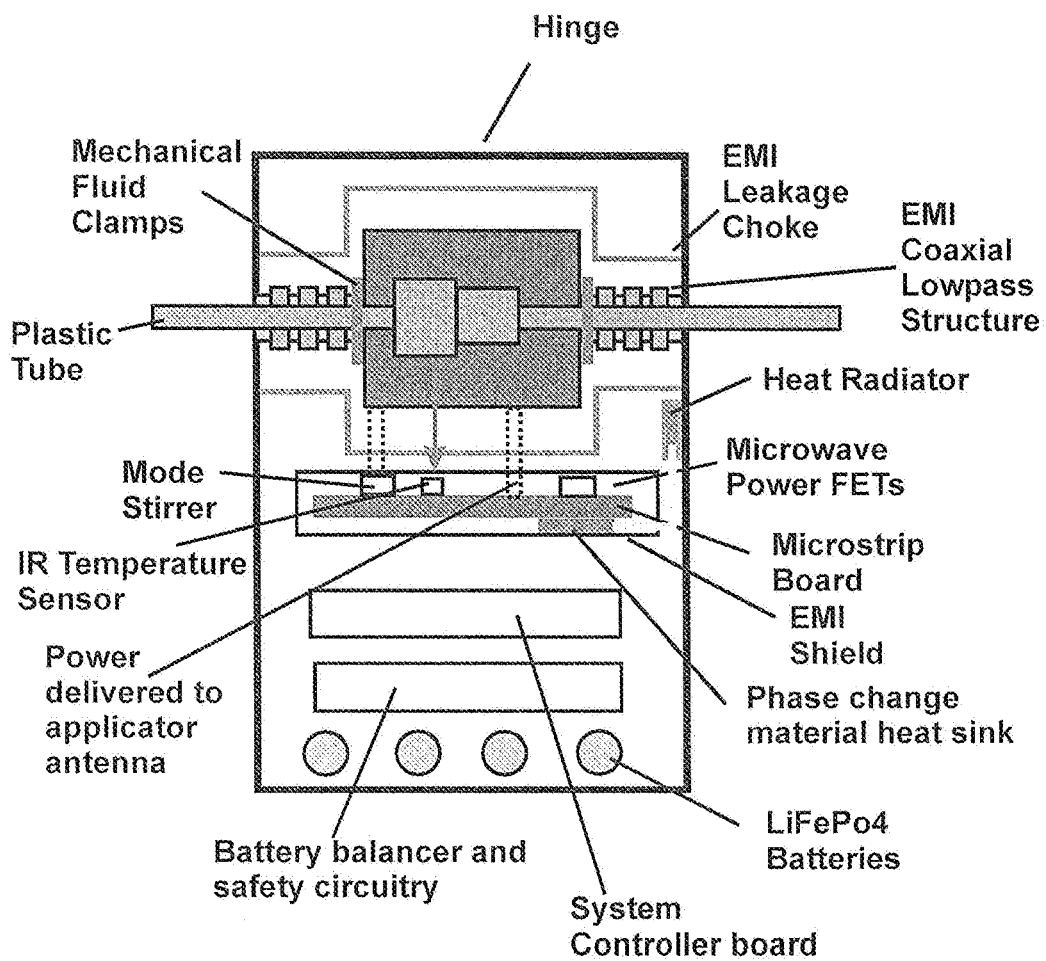
FIG. 1 is an overall view of the hand-held sterilizer and its chief components

A handheld device for applying this microwave energy is depicted in FIG. 1. A plastic tubing with a luer lock are placed inside of a microwave chamber. The chamber serves to focus the microwave energy on a fluid inside of the tubing, and to prevent RF leakage outside of the chamber. Mechanical fluid clamps engage on both sides of the tubing to seal off a short section. This allows pressure to build up, and consequently the water/saline solution temperature to exceed 100 deg. C. without boiling.

Directly underneath the microwave power transistor (FET) is a phase change material heat sink. Connected to that heat sink is a structure for slowly removing the heat to the outside of the handheld case via a Heat Radiator.

A good deal of waste heat will be generated during the short sterilization cycle. The heat will primarily be generated in the high power microwave FET device. Cooling of this device will involve the phase change material. Either a salt, wax, or liquid/gas (heat pipe) will absorb the energy during a six-second to one-minute sterilization event. Then during the relatively longer interval between sterilization events, the heat will be slowly transferred to the outside of the handheld case. In the case of a liquid/gas heat pipe, the radiating element on the case is elevated above the FET device location.

When the operator installs the plastic tubing/Luer Lock into the device, the cover is snapped closed. Simultaneously with latching the lid, mechanical clamps provide force to seal off a short length of the tubing for pressurization during heating. The controller decides when to release the clamps, and when to pop open the top cover.

An emergency override with independent circuitry and mechanical means allow the operator to cease the sterilization process, release the pressure, and then open the cover at any time. This overrode includes a fully redundant emergency stop feature that operates with independent electronic or mechanical means to disconnect the battery from the microwave high power source,) safely release the fluid pressure, and to open the top cover latch.

An IR Temperature Sensor monitors the real-time temperature of the liquid to be heated. A mode stirrer varies the electrical properties of the applicator antenna so that the electric field focus point can be dithered slightly to eliminate hot/cold spots in the liquid, thereby reducing heating time required.

Short application times will require temperatures significantly higher than 100 C. To achieve this in water or saline solution both ends of the plastic tubing are mechanically restricted. An infra-red thermometer chip monitors the temperature of the liquid to be sterilized and provides that information to the controller, which stops or reduces the RF power supplied to the applicator so that an over-temperature condition, which would result in too much internal pressure, cannot be reached. By monitoring the temperature of the liquid inside of the tubing, one can therefore monitor the internal pressure, and limit it to the optimal 2 to 3 atmosphere PSIG range. This is significant for safe operation of this device, particularly if one end of the tubing is attached to a patient intravenously. IR temperature can be measured through the plastic Luer lock or through the flexible tubing attached to it.

The battery pack is chosen as a LiFePo4 for its low out gassing potential, low susceptibility to overcharging or heavy discharging, and its high energy storage capacity. A battery balancer circuit is attached to each cell to insure that it is properly charged and to report health and status of the battery pack. Battery safety circuitry, including independent emergency power disconnect is also provided.

For handheld operation, a particularly useful power supply has seven or eight LiFePo4 cells, providing either 24 or 27 volt nominal operation. LiFePo4 cells provide the least chance of out gassing or overheating while providing a very high energy-storage capability. Cells in the 300 mA-H to 1.3 A-H capacity are optimal for single shift to multi-shift operation before a recharging event is required.

In a portable handheld device, the applicator elements are small. As a result, the optimal frequency for sterilization will be around 2400-2500 MHz.

FIG. 1 also shows a controller. Among the features of a typical controller are the ability to sterilize according to a sterilization profile (temperature vs. time) that can be varied to match the needs of each manufacturer's luer lock, and a real time monitor of the fluid temperature to assist in avoiding an over-temperature and over-pressure event.

There are expected to be various forms of tubing and Luer-Lock available for sterilization. The microcontroller will store accepted sterilization profiles for each. These profiles may include varying the time at temperature and the ultimate high temperature needed for sterilization (in order to be compatible with "softer" plastics that may not take the full temperature needed for quick sterilization). Other profile items would include information whether UV light should be on or off, which would depend on the plastic's UV tolerance, and whether the IR temperature monitor should be on or off, depending on whether the plastic is IR opaque or clear.

In some embodiments, the controller has a feedback loop to insure that adequate time and temperature has been applied to the liquid to assure sterilization.

The controller can have operator password protection so that only registered nurses or technicians can access the various profiles and alarm over-rides. Use of the emergency override will require the operator to re-enter the password before normal system operation re-commences.

The cover is self latching, and will not open until the sterilization cycle is completed, or unless the emergency override is pressed. The controller, in some cases, senses when the cover latch is closed, and continuously monitor the latch to ensure RF power is turned off upon detection of any anomaly concerning the integrity of the cover latch integrity during operation. Under normal operation, the controller decides when to release the fluid pressure, and when to later release the cover latch.

To manage the battery, the controller includes alarms to indicate battery over-voltage, under-voltage, misbalance, and overheating during use, as well as a monitor for storing the number of charge/discharge cycles and other battery monitoring data, including an estimate of remaining battery charge, and remaining lifetime of the battery pack before reconditioning in a non-volatile memory.

The controller in some embodiments will dictate when and for how long the pressure knife edge bars will be engages, and how much time before release of pressure to release of cover latch will transpire.

An optional feature of a controller is the ability to cause audible "beeps" to alert the operator to the occurrence of events such as the completion of sterilization, or the need to recharge or change the battery.

The on-board controller thus guarantees the safety of the sterilizer. IR thermometers monitor the fluid temperature while it is being sterilized. Also, a fail-safe timer is set so that no sterilization event can exceed to maximum time required for the sterilization profile used. If the fail-safe timer reaches its end count and the IR sensor has not yet recorded the proper temperature, an alarm is sounded, and the sterilizer goes into battery crowbar shutdown until an operating code is entered to re-start the unit.

Figure 2:
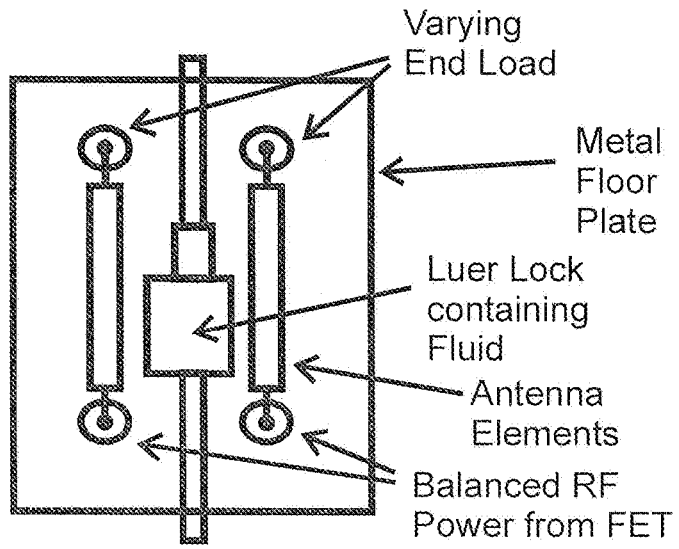
FIG. 2 shows balanced antenna elements, RF via holes from antenna to a printed circuit board containing a microwave source and load, and a Luer lock and tubing shown placed between the antenna elements.

Referring now to FIG. 2, a balanced field applicator is optimal for applying the RF energy to a liquid inside of a tubing element. Two antenna elements, one on either side of the liquid, concentrate the electric field most efficiently into the small sample size. A balanced field applicator has the least amount of RF leakage energy, so using this applicator technique reduces the need for EMI shielding methods.

Figure 3:
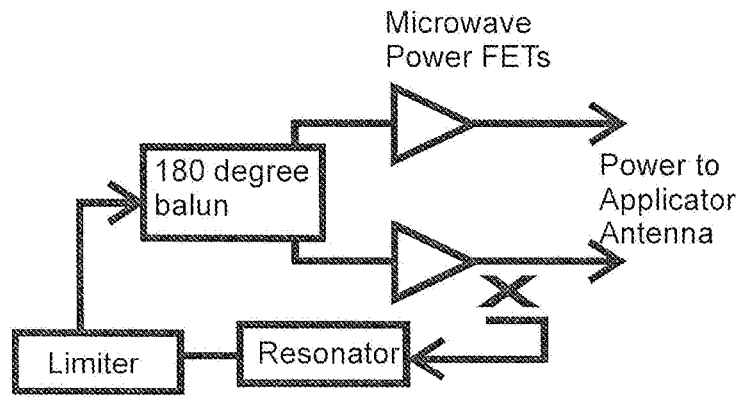
FIG. 3 is a block diagram of a circuit with two FET devices driving the applicator antenna out of phase.

Power is best generated by two devices, each driven by one arm of a 180 degree balun, coupler, or power divider. For example, FIG. 3 shows two FET devices driving the applicator antenna out of phase. Energy is coupled from one of the FETs, filtered in a frequency determining resonator, and fed back in the proper phase to form a self oscillating circuit. A limiter circuit protects the FET gate from severe overdriving, which would cause reliability problems.

Figure 4:
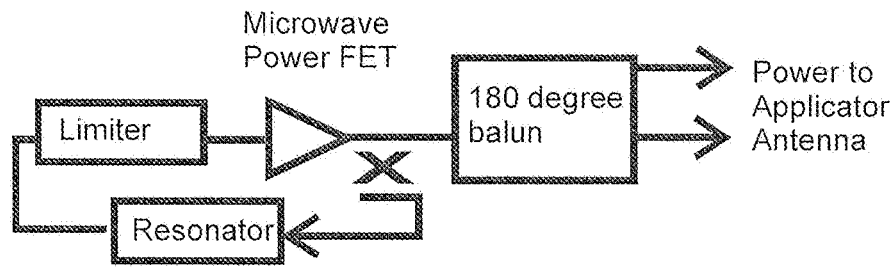
FIG. 4 is the circuit of FIG. 3 modified to use a single FET device.

For lowest cost, a single device may be used as a oscillator circuit, as shown in FIG. 4. A passive balun will be used at its output to generate the balanced twin signals needed for the applicator. A semiconductor or active limiter circuit is attached to the oscillator gate so that RF power levels are kept low enough to stop any forward conduction or run-away effects in the FET device.

In other embodiments, a separate oscillator driving a power amplifier stage and a passive balun can be used. Here a fixed attenuator pad or drive oscillator bias control is used to keep the power amplifier stage from any forward conduction or run-away effects in the FET device. The oscillator frequency can be dithered or varied over the 2400 to 2500 MHz range in order to provide a slightly shifting electric field maximum in the applicator sample area. This will assure fewer hot and cold spots in the liquid, and therefore a shorter sterilization time.

Figure 5:
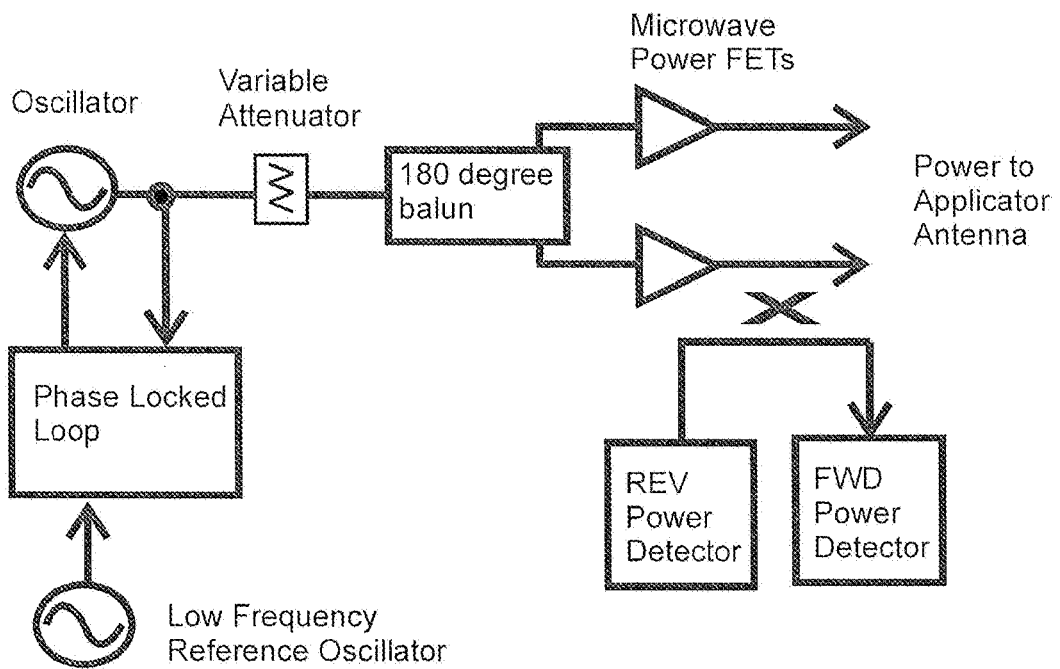
FIG. 5 shows an output stage driven by an independent oscillator.

FIG. 5 shows an example in which one of the output stages shown in FIGS. 3 and 4 is driven by an independent oscillator. The oscillator can have its frequency be voltage controlled by a phase locked loop circuit. The phase locked loop can set the oscillator to a precise frequency, or cause it to frequency hop (spreading its energy) by varying its divisor ratio. Alternatively, the low frequency reference can be chose to be a spread spectrum clock, spreading the microwave power over a wide frequency band. Spreading the frequency will improve RF leakage measurements and better comply with government required specifications. Frequency spreading will also minimize hot and cold spots in the liquid heating by varying the location of the electric field maximum.

A varying end load to the two balance applicator elements can be used to vary the electric field maximum location. PIN diodes or switched power FETs are used to vary the end load position, thereby varying the electric field maximum physical position. This will assure fewer hot and cold spots in the liquid, and therefore a shorter sterilization time.

Figure 6:
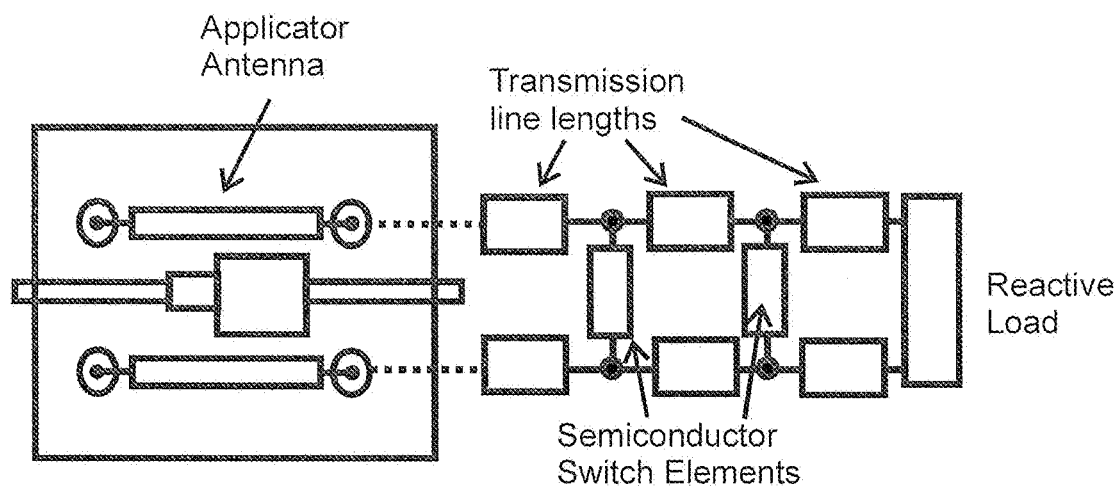
FIG. 6 shows an applicator antenna connected to a reactive load by transmission line lengths and switching elements.

Referring now to FIG. 6, after the energy is applied to the liquid sample, the ends of the applicator antenna may be attached to a varying load. The load consists of a loss-less end reactance and various lengths of transmission line. PIN diodes or FETs act as switches along the transmission line. The controller can vary the bias to the PIN diodes or FETS to cause them to act as microwave opens or shorts, thereby varying the electric field patterns in the vicinity of the liquid.

A pseudo-random frequency hopping sequence can be programmed into the oscillator so that the frequency jumps from one frequency to another after a short dwell time. This will help to meet RF leakage requirements in volts/meter by not jamming one specific frequency for any length of time.

Frequency hopping can be implemented by varying the control voltage on a varactor diode tuning a ceramic coaxial resonator.

Alternatively, a phase locked loop chip can be used to provide the control voltage to the varactor diode/ceramic resonator pair if more frequency precision is required. In this second method, the phase locked loop divisor ratio can be varied with time.

Alternatively the PLL low-frequency reference oscillator (crystal, SAW, or MEMs oscillator) can be a spread spectrum type of oscillator, with the PLL locking the microwave oscillator to form spread spectrum frequency steps.

The microwave applicator chamber is enclosed in metal. This metal can be machined metal, deep drawn sheet metal, or metal sputtered onto metal surface inside of a plastic outer housing. A microwave "choke joint" is present at the interface between the moveable cover and the main housing to suppress leakage of RF energy. Additional outer bands of microwave absorber material are embedded to the outside of this microwave choke joint to further reduce RF energy leakage.

RF energy might also leak out of the small cuts in the housing that allow mechanical passage of the plastic tubing. In some embodiments, a high-Z, Low-Z coaxial structure, similar to a waveguide "waffle-iron" filter is added to the housing structure to stop this leakage.

Figure 7:
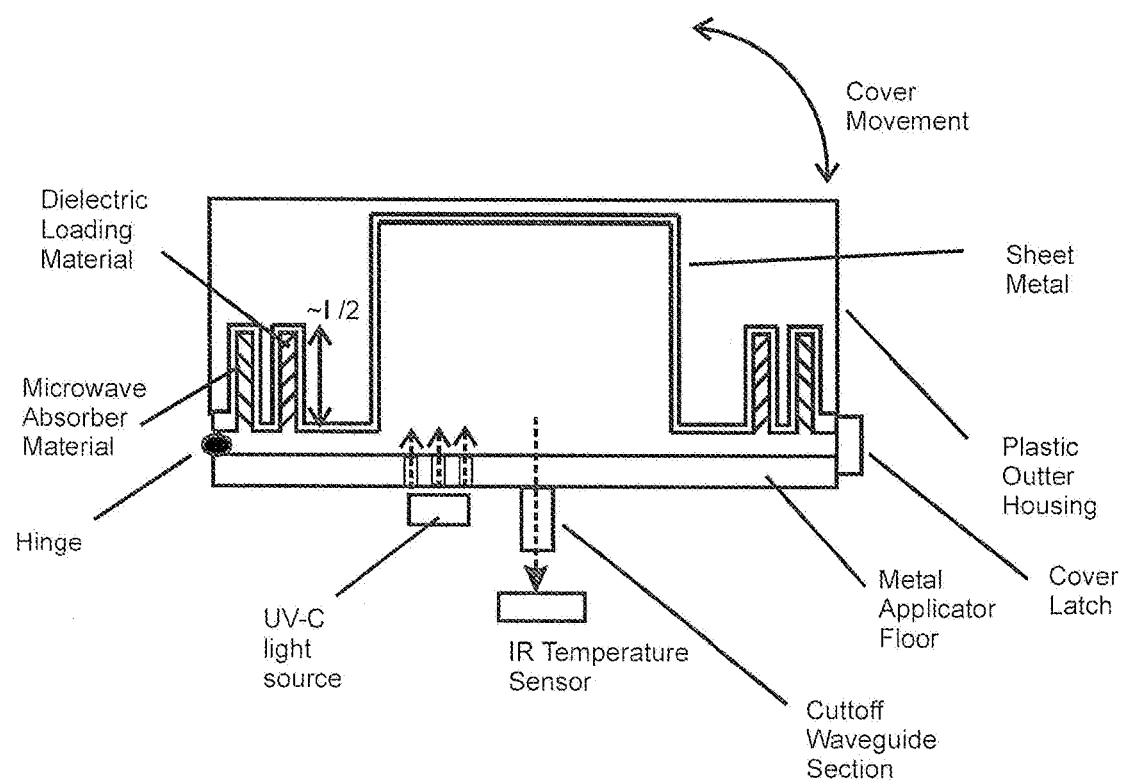
FIG. 7 shows the microwave application chamber.

Referring to FIG. 7, in one embodiment, the microwave application chamber is formed of two pieces of sheet metal. The bottom floor is relatively flat, with various small holes to pass microwave energy up or down to the microwave printed circuit board. The applicator antenna is not shown in FIG. 7.

Around the periphery of the top cover are deep drawn or machined "slots." The outer-most slot, which is about a quarter-wavelength deep, is filled with microwave absorber material. Inside this outer slot is an inner-slot filled with dielectric loading material. Microwave energy leakage from the applicator antenna is somewhat reduced already because the electric field is strongly concentrated between the two antenna elements (not shown in the figure).

Additional RF leakage energy incident on the crack between the top cover and bottom floor may escape the chamber. To suppress this, a first slot ring acts as a "microwave choke joint" that creates a short circuit at the deep end of the slot reflects back as another short circuit at the small gap between the cover and floor. To a void having an unreasonably long choke joint, which would be a half-wavelength deep, the choke joint is loaded with a high dielectric constant material. Next to the joint is another annular slot surrounding the cover. This slot is filled with an absorptive material. Once again, its length is approximately half wavelength, resonating at 2.45 GHz and causing the maximum absorption. In this manner, the RF leakage suppression from the cover requires neither a tight fit nor a microwave gasketing material.

Also shown in FIG. 7 is an IR temperature sensor. A short circular or rectangular section of "cutoff waveguide" allows the IR energy to pass thru unimpeded, but stops the high power microwave energy from leaking through. The circular or rectangular "pipe" between the applicator chamber and the IR thermometer chip thus act as a "cut-off waveguide" to limit RF energy from leaking out of the applicator chamber to damage the IR sensor.

FIG. 7 also shows an optional UV light source in the C band wavelength for use in disinfecting MRSA Staph bacteria and other difficult to kill organisms. The application of both microwave and UV-C sterilizing energy will do a better job than either by themselves. A series of small diameter holes is shown to allow the UV-C to pass through without the microwave energy leaking out. A fine metal mesh or perforated section of the applicator metal housing will also allow the UV light to bath the sample without RF energy escaping the chamber and damaging the UV light source. A user can use user-controls to shut off the UV-C energy for plastic devices that cannot tolerate the UV-C light. The UV-C light is generated using either a standard bulb or with light emitting diode.

Figure 8:
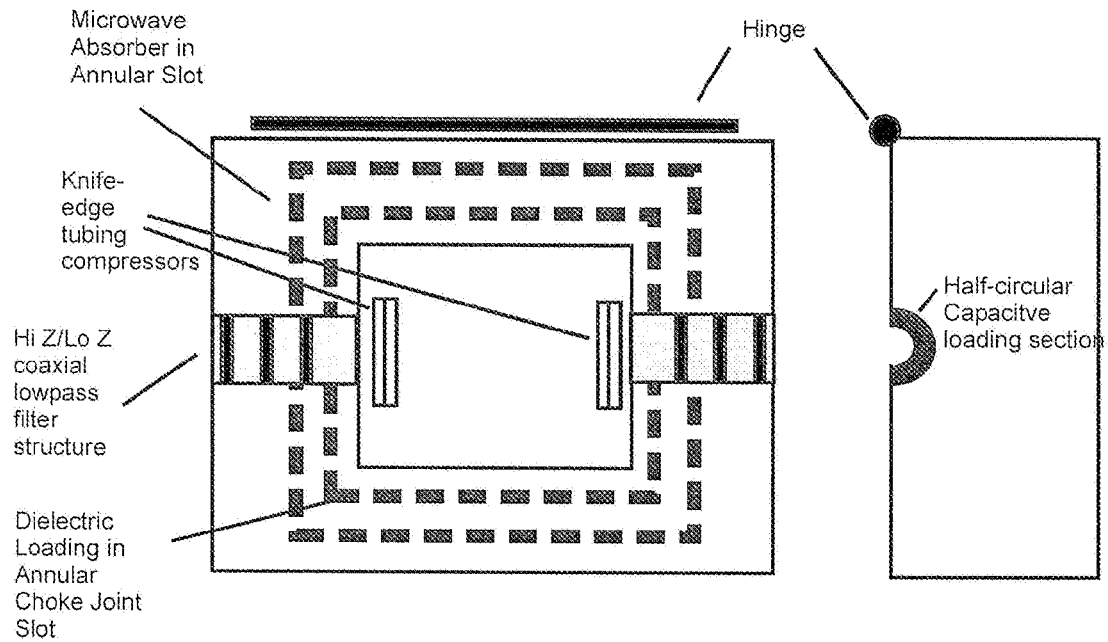
FIG. 8 shows inside and edge views of a moveable top

FIG. 8 shows inside and edge views of a movable top cover. Also seen in FIG. 8 is another depiction of the RF choke joint, which has an inner annular slot, and the microwave absorbing slot. The half-moon cutouts at either end show the Hi Z/Lo Z coaxial low pass filter structure referred to above. When the cover is closed and close to the flat floor plate, microwave energy is low-pass filtered as is travels from the inside to the outside of the box. Adding a fluid filled plastic tube inside of the two coaxial low pass structures does not impede this low pass filtering function.

Also shown in FIG. 8 are two knife-edge tubing compressor bars. As the top cover is closed and latched, these two bars compress the soft plastic tubing with sufficient force to maintain at least 3 atmospheres of pressure during the sterilization process. The two bars are spring loaded, and the force is able to be relieved by the system controller before the top cover is unlatched.

Figure 9:
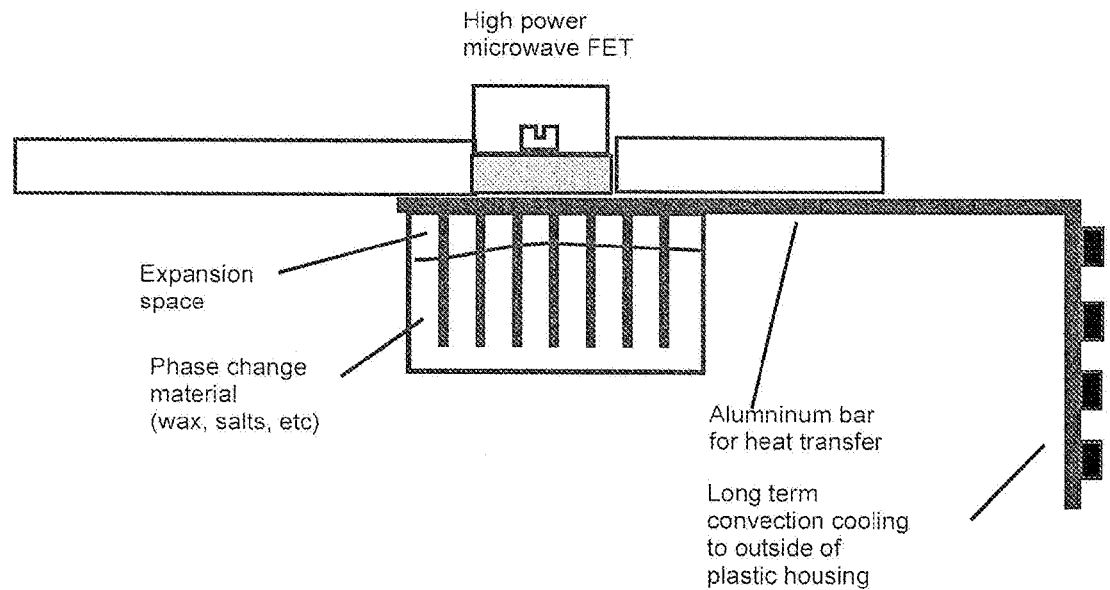
FIGS. 9 and 10 show cooling systems for the apparatus shown in FIG. 1.

FIG. 9 shows one embodiment of a cooling system. Since the microwave FET transistor is only on for brief periods of time with long periods of inactivity, a phase change material (PCM) heat sink is practical. A chamber with metal heat transfer fins is filled with either wax or other materials that would undergo a phase change in the required temperature range. The metal fins are intimately bonded to the bottom of the microwave FET transistor.

In operation, as the transistor heats up, the heat generated starts to melt the phase change material. Even if the unit is tipped over, because the PCM is confined to the chamber, it still will provide heat sinking of the FET. After the sterilizing event is completed, there is a long period of time, on the order of minutes, available for the heat stored in the PCM to conductively travel to a metal radiator at the outside of the unit package. By the time the next sterilization event happens, the PCM will be either partially or fully re-hardened to a solid and will thus be ready to absorb additional heat.

A temperature monitor (thermistor) attached to the PCM laden fins provides the controller a real time measurement of PCM material temperature. If the temperature rises too high (due to abnormally high sterilization usage), the controller will prevent the operator from engaging the unit until it has cooled down to normal range again.

Figure 10:
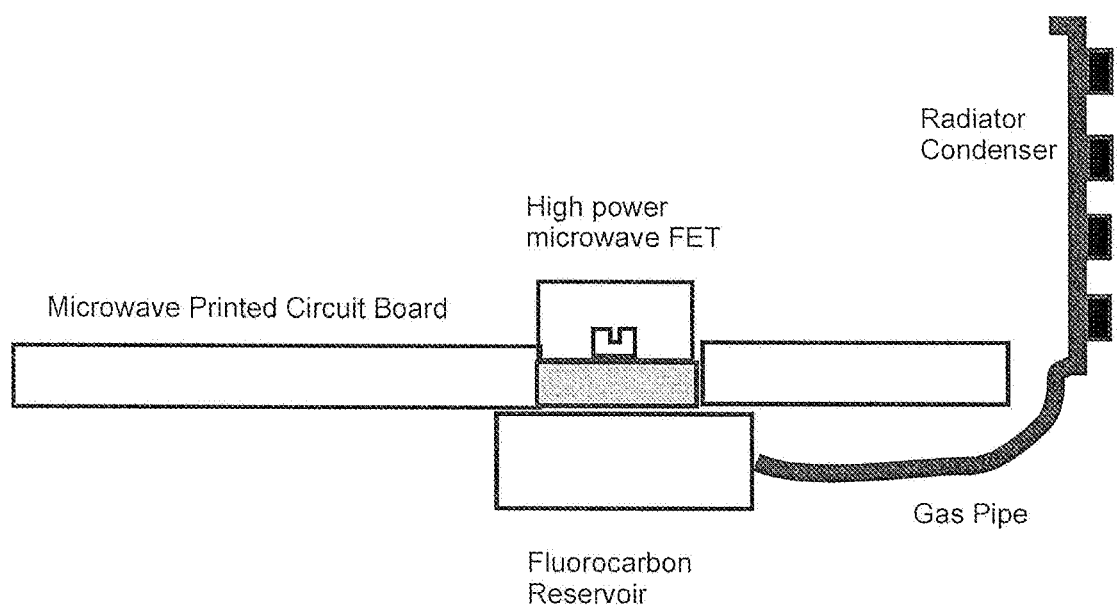

Another embodiment of a cooling system, shown in FIG. 10, relies on a fluorocarbon filled heat pipe. Fluorocarbon filled heat pipes can also be used to keep the transistor temperature from exceeding a specified safe limit. When the cooling system of FIG. 10 is used, the radiator/condenser plate is higher than the base of the FET transistor since gravity is used to cause flow of the condensed fluorocarbon back to the reservoir.

Having described the invention and a preferred embodiment thereof, what I claim as new and secured by Letters Patent is:

1. An apparatus for sterilizing a fluid fitting, said apparatus comprising a microwave source disposed in a shielded chamber, a pressure chamber inside said shielded chamber for receiving said luer lock and a sterilizing medium, said pressure chamber being in microwave communication with said microwave source, mechanical fluid clamps at each end of said pressure chamber for enabling pressurization of said pressure chamber, and a low-pass filter disposed to suppress leakage of microwave radiation, wherein said low-pass filter comprises a microwave choke having an outer ring shielded by a dielectric material loaded with a material selected from the group consisting of iron and carbon.

2. The apparatus of claim 1, further comprising a phase-change material disposed under said microwave source for absorbing energy from said shielded chamber for disposal outside said shielded chamber.

3. The apparatus of claim 1, further comprising an infra-red temperature sensor to monitor a temperature of said sterilizing medium within said pressure chamber.

4. The apparatus of claim 1, further comprising a mode stirrer for dithering a spatial location of a focal point of said microwave energy within said pressure chamber.

5. The apparatus of claim 1, wherein said microwave choke comprises joints filled with a dielectric material having a dielectric constant relative to free space of at least fifteen.

6. The apparatus of claim 1, wherein said dielectric material is loaded with iron but not carbon.

7. The apparatus of claim 1, wherein said dielectric material is loaded with carbon but not iron.

8. The apparatus of claim 1, wherein said microwave source comprises a self-oscillating transistor.

9. An apparatus for sterilizing a fluid fitting, said apparatus comprising a microwave source disposed in a shielded chamber, a pressure chamber inside said shielded chamber for receiving said luer lock and a sterilizing medium, said pressure chamber being in microwave communication with said microwave source, mechanical fluid clamps at each end of said pressure chamber for enabling pressurization of said pressure chamber, and an infra-red temperature sensor to monitor a temperature of said sterilizing medium within said pressure chamber.

10. The apparatus of claim 9, further comprising a phase-change material disposed under said microwave source for absorbing energy from said shielded chamber for disposal outside said shielded chamber.

11. The apparatus of claim 9, further comprising a mode stirrer for dithering a spatial location of a focal point of said microwave energy within said pressure chamber.

12. The apparatus of claim 9, further comprising a low-pass filter disposed to suppress leakage of microwave radiation.

13. The apparatus of claim 12, wherein said low-pass filter comprises a microwave choke having joints filled with a dielectric material having a dielectric constant relative to free space of at least fifteen.

14. The apparatus of claim 9, wherein said microwave source comprises a self-oscillating transistor.

15. An apparatus for sterilizing a fluid fitting, said apparatus comprising a microwave source disposed in a shielded chamber, a pressure chamber inside said shielded chamber for receiving said luer lock and a sterilizing medium, said pressure chamber being in microwave communication with said microwave source, mechanical fluid clamps at each end of said pressure chamber for enabling pressurization of said pressure chamber, and a mode stirrer for dithering a spatial location of a focal point of said microwave energy within said pressure chamber.

16. The apparatus of claim 15, further comprising a phase-change material disposed under said microwave source for absorbing energy from said shielded chamber for disposal outside said shielded chamber.

17. The apparatus of claim 15, further comprising a low-pass filter disposed to suppress leakage of microwave radiation.

18. The apparatus of claim 17, wherein said low-pass filter comprises a microwave choke having joints filled with a dielectric material having a dielectric constant relative to free space of at least fifteen.

19. The apparatus of claim 15, wherein said low-pass filter comprises a microwave choke having an outer ring shielded by a dielectric material loaded with a material selected from the group consisting of iron and carbon.

* * * * *